United States Patent [19]

Lipshutz

[11] Patent Number: 5,405,981

[45] Date of Patent: Apr. 11, 1995

[54] COPPER CATALYZED COUPLING REACTIONS

[75] Inventor: Bruce H. Lipshutz, Goleta, Calif.

[73] Assignee: The Regents of the University of California, Oakland, Calif.

[21] Appl. No.: 37,947

[22] Filed: Mar. 26, 1993

[51] Int. Cl.$^6$ .............................................. C07F 1/08
[52] U.S. Cl. ..................................... 556/112; 556/28; 556/53; 540/1
[58] Field of Search ................ 556/112, 28, 53; 540/1

[56] References Cited

U.S. PATENT DOCUMENTS

| | | | |
|---|---|---|---|
| 4,415,501 | 11/1983 | Grudzinskas et al. | 260/429.3 |
| 4,777,275 | 10/1988 | Campbell et al. | 556/112 |
| 4,785,124 | 11/1988 | Campbell et al. | 556/28 |
| 5,072,010 | 12/1991 | Lipshutz et al. | 556/112 |
| 5,166,382 | 11/1992 | Lipshutz et al. | 556/112 |

OTHER PUBLICATIONS

Noyori et al., "An Organometallic Way to Prostaglandins: The Three-Component Coupling Synthesis", *Chemtracts-Organic Chemistry*, 3:173-197 (1990).

Suzuki et al., "Three-Component Coupling Synthesi of Protaglandins", *Tetrahedron*, vol. 46 Nos. 13-14, pp. 4809-4822 (1990).

Tuckmantel et al., "1,4-Addition of Triorganozincates and Silyldiorganozincates to α,β-Unsaturated Ketones", *Chem. Ber.*, 119:1581-1593 (1986).

Wipf et al., "Transmetalation Reactions of Alkylzirconocenes: Copper-Catalyzed Conjugate Addition to Enones", *J. Org. Chem.*, 56:6494-6496 (1991).

Isobe et al., "Trialkylzinclithium-A New Reagent for Conjugate Addition to α,β-Unsaturated Ketones", *Chemistry Letters*, pp. 679-682 (1977).

Schwartz et al., "Hydrozirconation: A New Transition Metal Reagent for Organic Synthesis", *Angew. Chem. Int. Ed. Engl.*, 15:333-340 (1976).

Negishi et al., "Organozirconium Compounds In Organic Synthesis", *Synthesis*, pp. 1-19 (1988).

*Primary Examiner*—Arthur C. Prescott
*Attorney, Agent, or Firm*—Robbins, Berliner & Carson

[57] ABSTRACT

A general method for sequential addition of two substituents to an α,β-unsaturated ketone (enone), involving 1,4-conjugate addition of a desired substituent group to the enone to form an intermediate enolate, followed by electrophilic trapping of the enolate, wherein catalytic amounts of copper are employed in combination with another organometallic compound to effect the conjugate addition via a reactive cuprate reagent and yet provide an intermediate enolate species based on the other organometallic compound which is amenable to trapping by a suitable electrophile. Pursuant to this method, a true three-component coupling reaction can be effected starting from an alkyne, an enone, and an electrophile.

19 Claims, No Drawings

COPPER CATALYZED COUPLING REACTIONS

This invention was made with Government support under Grant No. GM-40287, awarded by the U.S. Department of Health and Human Services. The Government has certain rights in this invention.

BACKGROUND OF THE INVENTION

This invention relates to the fields of organic synthesis and organometallic chemistry. In particular, this invention relates to methods for the preparation of organic compounds through the sequential addition of substituent groups to a substrate molecule without isolation of intermediates.

The utility of organocopper complexes as reactive intermediates in a variety of synthetic reactions has been well known for decades. Particularly important reactions utilizing organocopper complexes in the formation of carbon-to-carbon bonds include addition reactions (such as 1,4-conjugate additions and carbocupration reactions) and substitution reactions (such as, for example, the displacement of halides, tosylates or mesylates and ring opening of epoxides). In such reactions, the organocopper complex formally serves as the source of a suitable carbanion for introduction into a target molecule by addition or displacement.

Early work in the field of organocopper chemistry involved treatment of either catalytic or stoichiometric quantities of a copper(I) halide with a Grignard (RMgX) or organolithium (RLi) reagent. The resultant products are either neutral organocopper reagents RCu(I) or copper(I) monoanionic salts $R_2CuM$ (M=Li or MgX), commonly referred to as lower order or Gilman reagents. Copper(I) cyanide is also an excellent precursor for the direct formation of lower order cyanocuprates RCu(CN)Li upon treatment with an equivalent of an organolithium. It is believed that the strength of the Cu-CN linkage accounts for the direct cuprate formation with one equivalent of the organolithium, rather than the metathesis that occurs with copper(I) halides to produce an equivalent of LiX.

While such lower order complexes have some direct synthetic applications, it has further been determined that reagents of this type can be composed of different ligands (i.e., $R=R'$). In other words, rather than forming a complex of the formula $R_2CuLi$ from two equivalents of the same RLi, different organolithium compounds can be used to provide a complex of the formula $R_TR_RCuLi$. In this manner, it is possible to conserve potentially valuable $R_TLi$. Successful exploitation of such complexes comprising two different ligands is based on the ability to control the selectivity of transfer of the desired ligand $R_T$ rather than the residual (or "dummy") group $R_R$ from copper to electrophilic carbon.

A particularly significant advance in the field of organocopper complexes has been the development of so-called "higher order" cuprates. For example, the admixture of two equivalents of RLi (or one equivalent each of $R_TLi$ and $R_RLi$) with copper(I) cyanide proceeds to the formation of a copper(I) dianionic complex or higher order cyanocuprate, $R_2Cu(CN)Li_2$. The cyano ligand, with its $\pi$-acidic nature, is believed to enable the copper to accept a third negatively-charged ligand in ethereal solvents (e.g., EtO and THF). Such higher order complexes, particularly those derived from two different organolithium compounds, have been successfully exploited as highly selective and efficient means of making key carbon-to-carbon bonds.

The use of cuprates in 1,4-conjugate addition reactions for introduction of unsaturated carbanions is especially attractive due to the complete control of double bond geometry in the reaction scheme. This is of particular significance, for example, in the synthesis of various prostaglandins via conjugate addition of an alkenyl moiety to the unsaturated ketone functionality of a substituted cyclopentenone.

The preparation of reactive vinylic organocuprate reagents has involved a limited number of typical reaction pathways. For transfer of a particular alkenyl side chain to a target molecule, vinylic halides (usually, the bromides or iodides) and vinylic stannanes have typically been employed as a precursor molecule. These precursor molecules are generally prepared from the corresponding acetylene and converted to the reactive copper reagents for use as synthetic intermediates.

Campbell et al. U.S. Pat. No. 4,777,275, the entire disclosure of which is hereby incorporated by reference, describes a process for preparing a higher order copper complex in which a ligand (designated $R_t$) which is desired in a subsequent synthetic organic reaction to form a new carbon-to-carbon bond is transferred in situ from a stannane compound to a first higher order copper complex to form a second higher order copper complex including the ligand. Of course, to employ this method it is first necessary to prepare specific vinyl stannanes by art recognized techniques. Such techniques generally call for the reaction of a suitable acetylene with, e.g., a trialkyl tin hydride. Unfortunately, the stannanes are generally quite toxic and do not react to afford only the desired regio- and stereoisomer; rather, a mixture of vinylstannanes which cannot be easily separated is usually obtained. Therefore, it would be advantageous to avoid such intermediates entirely if possible.

Preparation of suitable cuprate complexes from the corresponding halides is also problematic, particularly in the case of alkenylhalides. Formation of the desired cuprates is generally effected from the corresponding alkenyllithium compounds, which in turn are prepared by metal-halogen exchange (typically using two equivalents of highly pyrophoric and expensive -t-butyllithium) with the corresponding alkenylhalides or reaction of the halides with lithium metal. Preparation of the organolithium precursors via this latter method is typically tedious, and may result in low yields. Moreover, in the case of the alkenyl compounds, there may be some loss of double-bond stereochemistry.

According to Grudzinskas et al. U.S. Pat. No. 4,415,501, the disclosure of which is also hereby incorporated by reference, some of the potentially problematic issues associated with the chemistry involved in the formation of vinylic cuprate complexes are avoided by utilizing an alternative class of reagents. A class of alkenylzirconium reagents are described, which may be employed directly in various conjugate addition reactions. These alkenylzirconium reagents are prepared by reaction of the corresponding protected alkynol with dicyclopentadienyl zirconium chlorohydride; the latter is typically generated in situ by the reduction of dicyclopentadienyl zirconium dichloride in solution under an inert atmosphere. The thus-prepared alkenylzirconium reagents are described as moisture sensitive, and thus it is suggested that they are best prepared just prior to use. Reaction of the alkenylzirconium reagents with the target molecule for a conjugate addition is effected in the presence of a catalytic amount of a reduced nickel catalyst.

While the method of U.S. Pat. No. 4,415,501 obviates some of the potential problems associated with the formation of the reactive cuprates, it does so at the cost of yield and purity of the resultant products, as is immediately apparent from a review of Table II of the reference. Indeed, while the products of hydrozirconation reactions may be utilized in selected coupling reactions to form carbon-to-carbon bonds, there is no general established method for directly transferring these ligands to alpha, beta unsaturated ketones in a conjugate (i.e., 1,4-) sense. Therefore, the reference method using organozirconium compounds directly as reagents is limited in applicability and clearly unacceptable for the preparation of most products, in particular from relatively expensive optically-active intermediates, on a commercial scale.

Hydrozirconation of alkenes by zirconocene chloride hydride, followed by addition of one equivalent of enone and catalytic amounts of Cu(I) or Cu(II) salts (such as CuBr, CuI and CuCN) has been reported to lead to the corresponding 1,4-addition products in moderate to high yield [Wipf, P. et al., *J. Org. Chem.* 56, 6494 (1991)]. This method was demonstrated only in very simple systems (i.e., not in $\alpha$- or $\beta,\beta$-disubstituted cases) and only with alkylzirconocenes.

Lipshutz et al. U.S. Pat. No. 5,072,010, the entire disclosure of which is hereby incorporated by reference, discloses a method whereby higher order cuprate complexes of the type described in, e.g., Campbell et al. U.S. Pat. No. 4,785,124, are prepared by means of a transmetalation from a corresponding zirconocene intermediate. This process is particularly valuable with respect to the introduction of vinylic side chains such as are present at the 3-position on the cyclopentanone ring in prostaglandins (commonly referred to as the $\beta$ side chain), as it is possible in accordance with the present invention to proceed directly from the acetylenic precursor 1 via the reactive cuprate to the desired final product 2 in a one-pot operation without isolation of intermediates and in high yields (Scheme 1).

Scheme 1

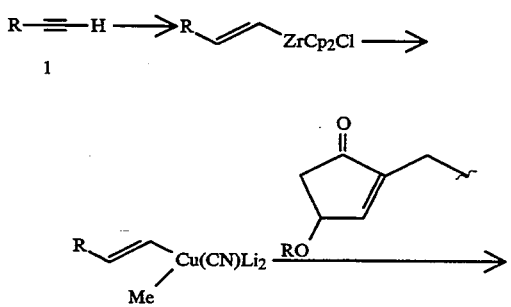

-continued
Scheme 1

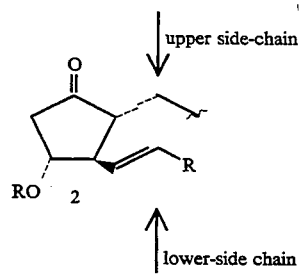

Thus, the problems associated with the preparation of the corresponding vinyl halide 3 or stannane 4 so as to provide an alkenyllithium 5 (Scheme 2) are avoided entirely.

Scheme 2

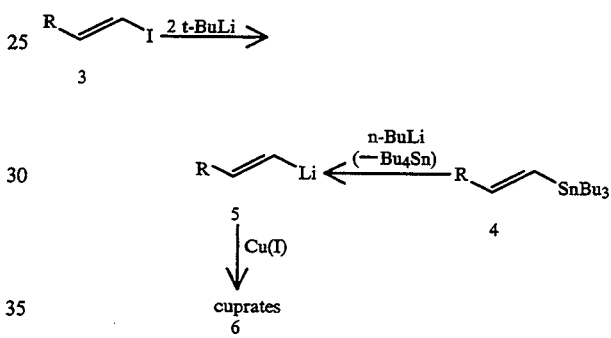

While the method disclosed in U.S. Pat. No. 5,072,010 is particularly attractive relative to the heretofore known approaches for preparation of organocuprates, the intermediate enolate formed using a cuprate as ligand source for a 1,4-conjugate addition has not been found to be susceptible to electrophilic trapping. As a consequence, preparation of a prostaglandin product as described in U.S. Pat. No. 5,072,010 requires that the side chain in the 2-position on the cyclopentanone ring (i.e., the upper or $\alpha$ side-chain) of the target prostaglandin be already in place in the cyclopentenone precursor.

It would be advantageous to provide a synthetic method in which 1,4-addition of, e.g., a vinylic cuprate to an enone would lead to an intermediate capable of subsequent trapping by an electrophile at the 2-position. As illustrated in Scheme 3, this would provide a method whereby introduction of side chains at both the 2- and 3- positions on the cyclopentanone ring of a target prostaglandin (i.e., the $\alpha$ and $\beta$ sidechains, respectively) could be accomplished in a single reaction sequence. As indicated, in such a sequence reaction of the cyclopentenone 7 with, e.g., a cuprate provides an intermediate 8, which in turn reacts with an electrophile (E+) to provide the desired prostaglandin product 9.

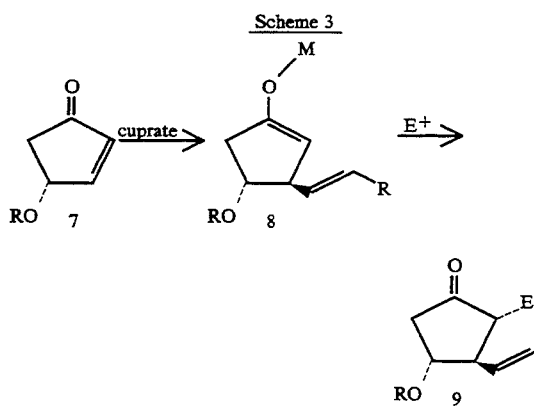

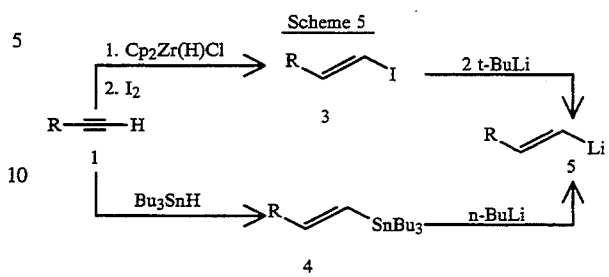

Several approaches have heretofore been proposed for a "three-component coupling" reaction of the type as generally illustrated in Scheme 3. One approach involves in situ formation of an organocopper reagent from equimolar amounts of copper(I) iodide and a vinyl lithium, with 2–3 equivalents of tributylphosphine, to effect a conjugate addition of the β side chain to the enone. As direct alkylative trapping of the resulting enone could not be attained in this form, triphenyltin chloride and HMPA are added; reaction then occurs with an α side-chain Z-allylic iodide [Suzuki, M. et al., *J. Am. Chem. Soc.* 107, 3348 (1985); Suzuki, M. et al., *J. Am. Chem. Soc.* 110, 4718 (1988)]. An alternative approach is through conjugate addition of the β side-chain in the form of a mixed zincate, (vinyl)Me$_2$ZnLi, to the enone 7 followed by enolate trapping using an α side-chain electrophile [Suzuki, M et al., *Tetrahedron* 46:4809–22 (1990); Noyori, R. and Suzuki, M., *Chemtracts—Organic Chemistry*, pp. 173–197 (May–June 1990)]. Pursuant to this method, an equimolar mixture of dimethylzinc and the β side-chain vinyllithium (forming the mixed zincate) is treated sequentially with the cyclopentenone 7 and an α side-chain propargylic iodide (in the presence of some HMPA) to form the desired fully-substituted product (Scheme 4).

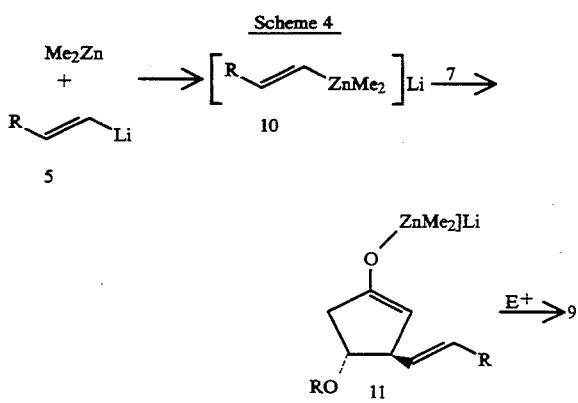

The β side-chain vinylic lithium is generated either by transmetalation between a tributyltin derivative and n-butyllithium, or by halogen-metal exchange between the corresponding vinylic iodide and t-butyllithium [Noyori, supra, at pp. 176–177]. Thus, in order to prepare the β side-chain precursor for use in the "three-component coupling" method developed by Noyori et al. from the corresponding acetylene, a plurality of steps (including purification and isolation of intermediates) is necessary (Scheme 5).

Pursuant to either approach for preparation of the β side-chain vinyllithium reagent 5, one thus confronts the same problems previously encountered with prior art routes for preparation of cuprates from the corresponding iodides or stannates (Scheme 2, supra).

The use of lithium triorganozincates in 1,4-conjugate addition reactions has been known for some time [Isobe, M. et al., *Chemistry Letters*, pp. 679–682 (1977)]. It has been recognized, however, that these reagents are not very reactive in 1,4-addition reactions; in many cases, either the desired addition reaction does not take place at all, or the yield of product is very poor [Tuckmantel, W. et al., *Chem. Ber.* 119:1581–93 (1986)].

It is an object of the present invention to provide a method for effecting an improved three-component coupling reaction, comprising a 1,4-conjugate addition to an enone followed by electrophilic trapping of the intermediate enolate, which does not suffer from the drawbacks attendant to the heretofore known methods.

SUMMARY OF THE INVENTION

In accordance with the present invention, there is provided a method for carrying out a 1,4-conjugate addition of a desired substituent group to an α,β-unsaturated ketone (hereinafter, "enone") to form an intermediate enolate, followed by electrophilic trapping of the enolate, wherein catalytic amounts of copper are employed in combination with another organometallic compound to effect the conjugate addition via a reactive cuprate reagent and yet provide an intermediate enolate species which is amenable to trapping by a suitable electrophile. Pursuant to this method, a true three-component coupling reaction can be effected starting from an alkyne (converted, for example, to a reactive cuprate species via the zirconocene, as described in U.S. Pat. No. 5,072,010) corresponding to a desired alkenyl group, an enone, and an electrophile.

DETAILED DESCRIPTION OF THE INVENTION

In accordance with the present invention, a protocol is provided which provides both the benefits of using a reactive and selective cuprate for 1,4-additions and the advantages of metal enolates other than copper (e.g., Zn, Mn, Ni) toward alkylation or 1,2-addition. Cuprates alone offer tremendous versatility not characteristic of any other class of organometallic. Moreover, their known ability to tolerate the presence of additives (e.g., BF$_3$.Et$_2$O, TMSCl) provides yet greater potential in cases where enone reactivity (due to steric factors or stereoelectronic effects) would otherwise preclude conjugate addition chemistry. On the other hand, the method permits one routinely to effect alkylation or 1,2-addition reactions of the in situ-formed, transmetalated enolates (e.g., of Zn), which could not be carried out as successfully using only copper reagents in a one-pot reaction.

Pursuant to the present invention, there is provided a novel method for the sequential introduction of groups $R_T$ and $R_E$ (as hereinafter defined) by reaction of suitable reagents with an enone of general formula $$R^A-C(O)-CH=CH-R^B$$

to prepare a compound of general formula $$R^A-C(O)-CHR_E-CHR_T-R^B$$

wherein $R^A$, $R^B$, $R_E$ and $R_T$ are as hereinafter defined, which method comprises:

forming a reactive cuprate solution comprising a catalytic amount of a reactive cuprate containing group $R_T$ and an organometallic compound comprising a metal which forms a more reactive enolate than a corresponding enolate derived from the cuprate;

reacting the reactive cuprate solution with the enone to introduce group $R_T$ and form a reactive enolate by exchange between copper and the organometallic compound; and trapping the reactive enolate with an electrophile precursor to $R_E$.

Pursuant to a preferred embodiment of the invention, the reactive cuprate solution is formed by:

reacting a precursor to $R_T$ with $Cp_2Zr(H)Cl$ and then $R^2Li$ to form an intermediate zirconocene containing group $R_T$; and reacting the intermediate zirconocene with a catalytic amount of a cuprate source to form the reactive cuprate in the presence of the organometallic compound comprising a metal which forms a more reactive enolate to form the reactive cuprate solution.

The precursor to $R_T$ suitably comprises an alkyne, in particular a 1-alkyne. The electrophile precursor to $R_E$ suitably comprises either an organic residue bearing a leaving group, or a carbonyl derivative. A method for 1,4-addition of a group $R_T$ to an enone comprising reacting the aforementioned reactive cuprate solution with the enone to introduce group $R_T$ is also provided.

The groups $R^A$ and $R^B$ in the enone represent the balance of the molecule which is not involved in the reaction sequence of the present invention. These groups may individually represent a wide variety of structures, and the exact definitions of $R^A$ and $R^B$ are not critical to the present invention. In general, $R^A$ and $R^B$ may comprise any structures which would not be prone to reaction with the reagents employed in introducing the $R_T$ and $R_E$ substituents. Exemplary groups, which are unsubstituted or substituted by one or more non-interfering substituents (as hereinafter defined) include alkyl of 1 to about 20 carbon atoms (including cycloalkyl); aryl, such as phenyl, naphthyl and phenanthryl; and aralkyl. In addition, $R^A$ and $R^B$ together with the balance of the molecule may form a cyclic enone; for example, $R^A$ and $R^B$ together may represent two unsubstituted or substituted methylene units (to form the corresponding 2-cyclopentenone) or three methylene units (to form the corresponding 2-cyclohexenone).

The reactive cuprate solution may comprise as the species active in the 1,4-addition a cuprate complex as described in Lipshutz et al. U.S. Pat. No. 5,072,010 of the general formula I

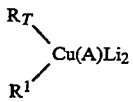

wherein $R_T$ is a ligand (as hereinafter defined) which will participate in carbon-to-carbon bond formation; $R^1$ is different from $R_T$ and is selected from the group consisting of alkyl, alkenyl, alkynyl, allylic, aryl, benzylic and heterocyclic moieties, $-BR^3$ wherein B is O or S and $R^3$ is an alkyl, alkenyl, alkynyl, allylic, aryl, benzylic or heterocyclic moiety, and $-NR^4R^5$ and $-PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents; and A is CN or SCN. Alternatively, a traditional copper complex usually prepared from CuX, wherein X is I, Br, Cl or OTf (triflate), of the formula $R_TR^1CuLi$ may be employed. Related cuprates (e.g., $R_TR_2^1Cu_2Li$, $R_TR_4^1Cu_3Li_2$, etc.) may also serve as active species in 1,4-addition reactions. These cuprates are believed to be continuously formed in the reaction mixture comprising the organometallic compound (upon reconstitution of the catalytic amount of cuprate source present in the mixture, as hereinafter described) by a transmetalation with the intermediate zirconocene and reacts with suitable enones in a manner essentially as described in U.S. Pat. No. 5,072,010.

In addition, in accordance with the present invention the reaction mixture for 1,4-addition to the enone contains an organometallic compound comprising a metal which ultimately serves to trap the enolate in a form in which it remains reactive to electrophiles and also serves as a source of $R^1$ to replenish $R^1$ groups onto the Cu(I) of the cuprate source after reaction with the enone. Transfer of an $R^1$ group to copper is required in order to regenerate the cuprate source involved in transmetalation from zirconium to copper, as described in detail in U.S. Pat. No. 5,072,010. The organometallic source of $R^1$ suitably comprises an alkyl metal lithium of formula $R_n^1MLi$, wherein M is a metal ion which forms an enolate which is more reactive toward electrophiles without resorting to additives (e.g., HMPA, etc.) than the corresponding enolate derived from the cuprate and n is an integer corresponding to the oxidation state of the metal ion plus 1. Suitable metal ions M include $Zn^{+2}$, $Mn^{+2}$, $Ni^{+2}$, $Sn^{+4}$, $Ti^{+4}$, $Fe^{+3}$, $Co^{+3}$, $Co^{+3}$, $Ag^{+1}$, $Ge^{+4}$, $Zr^{+4}$, and $Cd^{+2}$, all of which form more reactive enolate species than the corresponding copper/lithium enolates (the precise nature of the enolate formed from cuprate 1,4-additions not being as yet understood). All $R^1$ may be the same or different. In most cases, $R^1$ is methyl, as such materials (or suitable precursors thereto) are generally commercially available. For example, the trimethylzinc lithium compound may suitably be formed by reaction of a commercially-available $ZnCl_2$ (or the less hygroscopic $ZnCl_2$·TMEDA) with three equivalents of commercially-available methyllithium.

In a particularly preferred embodiment of the inventive method, a catalytic amount of a cuprate precursor (e.g., CuCN) and a precursor salt to the organometallic compound comprising M (e.g., $ZnCl_2$·TMEDA) are mixed together, followed by addition of the correct amount of $R^1Li$ (most suitably, MeLi) to form a mixed metal solution comprising $R_3^1ZnLi$ and a catalytic amount of $R_2^1Cu(CN)Li_2$. Alternatively, commercially available $R_2^1M$ salts (e.g., $Me_2Zn$) can be employed to form a mixed metal solution. A solution prepared in this manner may then be mixed with a solution comprising the intermediate zirconocene to form, via transmetalation, the reactive cuprate solution. The higher order cuprate solution comprising $R_2^1Cu(CN)Li_2$ may be stored in a refrigerator at about 0° C. almost indefinitely. Moreover, in preparation of such a mixed metal solution, $R^1Li$ can be used as supplied commercially either in diethyl ether or in THF/cumene (which is generally much safer to use).

The first step of a preferred embodiment of the claimed three-component coupling method employing as reactive cuprate species a compound of general formula I is reaction of the precursor to $R_T$ (e.g., an acetylene) with $Cp_2Zr(H)Cl$ to form a zirconium intermediate of general formula II

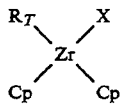

II wherein Cp represents a cyclopentadienyl moiety which is unsubstituted or substituted by non-interfering substituents (e.g., pentamethylcyclopentadienyl), X is halogen (e.g., Cl, Br, I) and $R_T$ is as hereinafter defined, is treated by addition of a compound of general formula $R^2M$ (e.g., $R^2Li$ or $R^2MgX$), wherein M is a suitable metal, X is halogen and $R^2$ is defined in the same manner as $R^1$ and may be the same as or different from $R^1$, to prepare an intermediate of general formula III

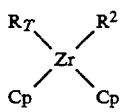

III wherein $R_T$ and $R^2$ are as previously defined.

Without isolation, the intermediate of general formula III is then reacted with an organometallic source of $R^1$ and a catalytic amount of a cuprate reagent (e.g., a compound of formula $R_2^1Cu(A)Li_2$) to provide a cuprate solution containing a catalytic amount of a reactive species for 1,4-addition the compound of general formula I via transmetalation from the zirconium intermediate. As an alternative to the above procedure, sequential additions of the elements of $R_2^1Cu(A)Li_2$ is also contemplated as within the scope of the present invention. For purposes of clarity, the following discussion will refer to R', defined in the same manner as $R^1$. As $R'_2Cu(A)Li_2$ is composed of 2 R'Li plus Cu(A), cuprate I can be prepared via addition of two equivalents of R'Li to intermediate II, followed by introduction of one equivalent of R'Cu(A)Li. Yet another variant procedure calls for addition of three equivalents of R'Li to zirconocene II, followed by one equivalent of Cu(A), the latter as a solid or in a LiX-solubilized form [e.g., Cu(A).nLiX, wherein n is an integer from 1 to 10] in solution in an ethereal solvent. Moreover, it is clearly not essential that, ultimately, three equivalents of the same R'Li be used; various combinations of organolithium reagents are acceptable. As explained in greater detail in U.S. Pat. No. 5,072,010, all of these alternatives proceed from the zirconocene II and the overall reaction pursuant to each alternative is believed to involve at least some transmetalation from zirconium to copper. Similarly, various combinations of components leading to a desired copper halide-derived cuprate may be employed (e.g., $R_2^1CuLi$, or $R^1Cu+R^1Li$, or $2R^1Li+CuX$, etc.).

Contrary to the method disclosed in U.S. Pat. No. 5,072,010 (which calls for an essentially stoichiometric amount of copper), in accordance with the method of the present invention the cuprate source as described above is provided in an amount substantially less than an amount equivalent to the amount of enone and/or zirconium used to prepare the zirconium intermediate III. Rather, only a catalytic amount of cuprate source is sufficient for carrying out the desired addition of ligand $R_T$ to the enone upon recycling of the copper, as hereinafter described. For any given reaction, an appropriate catalytic amount of cuprate source may readily be determined empirically. Typically, the amount of cuprate source employed is between about 1 mol-% and about 20 mol-%, preferably about 5 mol-% to about 20 mol-%, based on the enone and/or zirconium, although lesser amounts may be used depending upon the enone and the $R_T$ group in question.

The organometallic source of $R^1$ is employed in an amount sufficient to provide at least one equivalent of the metal M for every equivalent of enone and/or zirconium. Unlike the cuprate source (which is continuously regenerated by an exchange with the organometallic source of $R^1$), the organometallic source of $R^1$ is not regenerated after reaction of the enolate with an electrophile and work up of the product. A particular advantage of the use of a reduced amount of copper is the corresponding reduction in residual copper for disposal upon completion of the entire reaction sequence; while some residual copper salts are produced upon work-up of the product, the amount of copper is substantially reduced (i.e., in most cases by $\geq 95\%$) relative to use of stoichiometric amounts of copper. In contrast to copper, metals such as Zn and Zr are not major environmental concerns; both form strong M—O bonds, and are not an issue in work-up of the final product (as they are likely to form water-soluble, inert salts).

The catalytic amount of copper used in accordance with the method of the present invention is sufficient to enhance 1,4-addition via the more reactive cuprate complex, rather than with less reactive metallic species (such as the zincates employed in the three-component coupling reaction disclosed by Noyori et al.). It is clear that the cuprate is the reactive species, as the zirconocene of general formula III is inactive at −78° C. and transmetalation of $R_T$ from the zirconocene to the compound comprising metal M (e.g., $Me_3ZnLi$) is not, in general, efficient. Moreover, although other organometallic complexes (e.g., zincates) have been observed to react with unhindered enones, such complexes would not be suitable for use with substituted cases.

Upon 1,4-addition of the cuprate to the enone, a relatively unreactive enolate is formed bearing the copper/lithium as gegenion. While not wishing to be bound to any particular mechanism, it is believed that pursuant to the method of the present invention an exchange then occurs between the copper/lithium of the enolate and the metal M of the source of $R^1$, whereby M replaces copper in the enolate and an $R^1$ is transferred to the copper to regenerate the cuprate source. The regenerated cuprate source is thus available to react with another equivalent of the zirconium intermediate III to form more of the reactive cuprate I. The more reactive enolate formed with metal M then reacts with an electrophile E+(which is suitably added directly to the reaction mixture without isolation of the enolate) to provide the desired final product.

The zirconium intermediate of general formula II may be prepared in a manner known per se by a hydrozirconation reaction which comprises reacting a suitable ligand precursor compound (as hereinafter defined) for the carbanion $R_T$ with a compound of the formula $Cp_2Zr(H)Cl$, wherein Cp is as previously defined. Typically, Cp represents an unsubstituted cyclopentadienyl moiety, in which case the compound of the formula $Cp_2Zr(H)Cl$ corresponds to the well-known Schwartz reagent for hydrozirconation. Alternatively, the zirconium intermediate may be prepared by other methods known per se. Similarly, it is believed that in some instances, the vinyl zirconocene could also be prepared by reaction of a vinylic organometallic with a compound of general formula $Cp_2ZrCl_2$.

In addition to the preferred transmetalation from zirconium, it is known that transmetalations to copper can be effected from other organometallics. As previously noted, U.S. Pat. No. 4,777,275 describes transmetalations from stannanes to copper. In addition, similar transmetalations are known from vinyl alanes (e.g., $R_TAlR_2^1$) and vinyl tellurides ($R_TTeR^1$). While such transmetalations are contemplated as generally within the scope of the present invention, for the reasons given in detail in U.S. Pat. No. 5,072,010 the use of zirconium intermediates is presently considered to be particularly advantageous.

In the above formulas, $R_T$ represents a ligand corresponding to a chain or cyclic array which it is desired to introduce into a final product. As is well recognized in the art, an extremely wide variety of ligands for use in reactions such as 1,4-conjugate additions and displacements may be introduced into the known reactive cuprate species employed in accordance with the present invention (such as, for example, the higher order reactive cuprate complexes of general formula I). In particular, the ligands $R_T$ in accordance with the present invention comprise a broad range of structures that may be transferred in situ from a zirconocene complex to replace an alkyl ligand in a cuprate complex in accordance with the method of the present invention. Exemplary classes of ligands are, for example, those discussed in the aforementioned U.S. Pat. No. 4,777,275. Ligands $R_T$ of interest include: alkyl, such as straight or branched-chain alkyl and typically comprising one to about 20 carbon atoms, or cycloalkyl of three to about 20 carbon atoms; alkenyl, such as terminal and/or internal olefins and typically comprising two to about 20 carbon atoms, or cycloalkenyl of three to about 20 carbon atoms; aryl, such as phenyl, naphthyl and phenanthryl; allylic; and benzylic moieties. Of particular interest for purposes of the method of the present invention are those ligands $R_T$ which contain at least one unsaturation in the ligand carbon chain. The electronic configuration of such ligands apparently makes them particularly susceptible to the desired transmetalation from zirconium to copper. Ligands $R_T$ selected from the group consisting of terminal alkenyl, aryl, allylic and benzylic ligands are preferred for use in accordance with the present invention. Ligands $R_T$ comprising the beta side chain of a natural or synthetic prostaglandin are of particular interest. In such side chains, any hydroxy groups present are generally protected from undesired side-reactions in a manner heretofore known per se (for example, by trialkylsilyl, tetrahydropyranyl or tetrahydrofuranyl moieties).

In accordance with a preferred embodiment of the present invention, the provision of ligand $R_T$ may suitably be carried out by selection of a ligand precursor compound which provides the desired ligand via a hydrozirconation reaction with a compound of formula $Cp_2Zr(H)X$ in a manner known per se [see, e.g., Schwartz, J. et al., *Angew. Chem. Int. Ed. Engl.* 15(6), 333 (1976)]. For example, reaction of a 1-alkynyl compound results in the formation of an intermediate comprising the corresponding 1-alkenyl ligand (i.e., a vinylzirconocene); similarly, reaction of a 1-alkenyl precursor provides an intermediate comprising the corresponding alkyl ligand (i.e., an alkylzirconocene). The use of non-terminal alkenyl carbanion precursor compounds generally results in the formation of zirconocenes by placement of the zirconium moiety at the sterically least hindered position of the precursor chain as a whole, for example by Zr—H addition to an internal multiple bond followed by rapid rearrangement via Zr—H elimination and re-addition to place the metal in each case at the less hindered position of the alkyl chain. Hydrozirconation of 1,3-dienes proceeds by 1,2-addition to the sterically less hindered double bond to give gamma, delta-unsaturated alkylzirconium complexes in high yield; similarly, hydrozirconation of conjugated enynes to produce dienylzirconium derivatives has also been shown to proceed as predicted. In general, the products of such reactions are determined by size exclusion phenomena based primarily on steric effects. In some instances, the alternative procedures discussed supra and/or other known procedures for preparation of the zirconium complexes of general formula II (such as transmetalation or oxidative addition) may also suitably be employed to provide a particular anionic ligand $R_T$ (see, e.g., Negishi, E. et al., *Synthesis*, 1988, 1).

In a particularly preferred embodiment of the present invention, the zirconium intermediate of general formula II is prepared by reaction of a compound of the formula $Cp_2Zr(H)Cl$ with a 1-alkynyl compound of general formula $R-C\equiv C-H$, wherein R is selected from the group consisting of alkyl, alkenyl, aryl, allylic and benzylic moieties, said moiety being unsubstituted or substituted by non-interfering substituents (as hereinafter defined). In this manner, it is possible to prepare higher order cuprates comprising valuable vinylic ligands (for example, those corresponding to the beta side chains characteristic of prostaglandin analogs) directly from the corresponding 1-alkynes. A particular advantage of this preferred embodiment of the invention is that it is unnecessary to isolate the zirconium intermediate of general formula II from the reaction mixture in which it is formed.

After formation of the intermediate zirconocene of general formula II, in accordance with a preferred procedure as described in U.S. Pat. No. 5,072,010 addition to the reaction solution of one equivalent of $R^2Li$ is generally carried out at low temperatures (e.g., about $-78°$ C.) to form the intermediate of general formula III. A cooled solution containing $R_2^1Cu(A)Li_2$ (prepared, for example, by the reaction of two equivalents of $R^1Li$ with CuCN in a suitable solvent) or a combination of components equivalent thereto is added and the solution stirred at $-78°$ C. for a relatively short period of time (e.g., approximately 15 minutes).

Following the transmetalation to form a catalytic amount of the mixed higher order cuprate of general formula I, the reagent mixture is employed directly in a 1,4-addition reaction with a suitable enone. Suitable solvents include tetrahydrofuran (THF), substituted tetrahydrofuran, dimethyl ether, diethyl ether, dimethoxyethane (DME), dimethyl sulfide (DMS), methylene chloride, toluene, benzene, dibutyl ether and -t-butyl methyl ether. The cuprate complex of general formula I may suitably be used in the presence of one or more additives. Exemplary additives include Lewis acids, such as boron trifluoride etherate ($BF_3 \cdot Et_2O$); silyl halides, such as trimethylsilyl chloride ($Me_3SiCl$); phosphines, such as tri-n-butylphosphine (n-$Bu_3P$); amines, such as tetramethylethylenediamine, TMEDA ($Me_2NCH_2CH_2NMe_2$); and various alkali metal salts, including halides and alkoxides (e.g., lithium halides or alkoxides, LiX/LiOR).

Reaction of the enone with the higher order cuprate complex formed in accordance with U.S. Pat. No. 5,072,010 occurs rapidly to form a copper/lithium enolate. As the cuprate source is employed in only a catalytic amount, pursuant to the present invention the organometallic compound comprising the metal M which serves to trap the enolate in a form in which it remains reactive to electrophiles undergoes an exchange with the copper, thereby forming a more reactive enolate bearing M as gegenion and providing a regenerated cuprate source to engage in transmetalation with another molecule of the zirconocene. While the mechanism of this exchange is not entirely understood, it is believed to involve transfer of one $R^1$ group to copper from M (thereby regenerating the cuprate source); the more reactive enolate formed with the balance of the organometallic compound comprising M (the M-enolate) is then available for reaction with a suitable electrophile.

Reaction of the M-enolate with a suitable electrophile which serves as a precursor to $R_E$ is carried out in a manner known per se. One class of known electrophiles which may serve as precursor to $R_E$ includes compounds of the formula $R_EX'$, wherein X' is a suitable leaving group; typically, X' is a halide, especially the iodide. Another class of known electrophiles which may serve as precursor to $R_E$ includes aldehydes of the formula $R_E'CHO$, in which the 1-position carbon of $R_E$ is derived from the carbon of the aldehyde group and $R_E'$ represents the balance of $R_E$. Thus, $R_E$ has the general structure $R_E'CH(OH)$— upon reaction of the aldehyde $R_E'CHO$ with the enolate. Other suitable electrophiles as are well known in the art include, but are not limited to, the following: acylating agents (e.g., acid halides, anhydrides, etc.); $\alpha,\beta$-unsaturated nitro compounds (i.e., nitroalkenes); epoxides; and vinyl sulfoxides and sulfones. In general, the reaction of electrophiles with enolates is well known in the art and is regarded as part of the invention only insofar as it constitutes part of the overall sequence. As was the case with $R_T$, a wide variety of structures are encompassed by suitable $R_E$ groups; one of the advantages of the inventive method is its broad applicability to a wide range of synthetic reaction schemes. For proposes of the present invention, $R_E$ is defined in the same manner as $R_T$; as was the case with $R_T$, it is of course appropriate that substituent groups other than the one involved in the addition to the enolate be properly protected to avoid undesired side-reactions. Of particular interest are those $R_E$ groups corresponding to the $\alpha$ side-chain of a prostaglandin or related prostanoids (e.g., prostacyclins), which may be employed for synthesis of prostaglandins or related prostanoids in a true, three-component coupling reaction.

In a particularly preferred embodiment of the present invention, the entire synthetic process is carried out without isolation of any intermediates in a one-pot reaction starting from a suitable 1-alkyne. This preferred embodiment is illustrated in Scheme 6 in an exemplary synthesis of a prostaglandin-type compound. Alkyne 1 is reacted with $Cp_2Zr(H)Cl$ to form zirconium intermediate 12. This is in turn reacted with 1 equivalent of $R^1Li$ and a catalytic amount of a cuprate source and the exemplary organozinc lithium compound depicted in Scheme 6 to form a mixed metal solution containing at least some of the reactive cuprate species 13. Upon addition of cyclopentenone 7 to the mixed metal solution, the expected 1,4-addition occurs with transfer of the vinylic ligand from the cuprate and formation of the enolate 14. As enolate 14 is relatively unreactive towards many electrophiles, it is believed that an exchange occurs between the enolate and the organometallic lithium compound containing M (e.g., the zinc compound illustrated in Scheme 6). In this exchange process, one $R^1$ group (here, methyl) is transferred to the copper to regenerate the cuprate source; the regenerated cuprate source is then available to react with zirconocene 12 to generate more of the reactive cuprate 13. In addition, enolate 11 is formed with the metal M (e.g., the zinc compound in Scheme 6). This more reactive enolate 11 then reacts with the electrophile $E^+$ to form the desired final product 9.

As can be seen from Scheme 6, at no stage of the reaction procedure is it necessary to isolate any intermediates. Moreover, the use of mixed metals makes it possible to take advantage both of the higher reactivity in 1,4-additions of the cuprate 13 (relative to, e.g., the corresponding zincate) and of the higher reactivity in electrophilic addition of the zinc enolate (relative to, e.g., the corresponding copper/lithium enolate). Finally, the use of only catalytic amounts of copper significantly reduces problems which may be associated with the use of equivalent amounts of copper and zirconium (in particular, with respect to disposal of copper salts after completion of the reaction sequence).

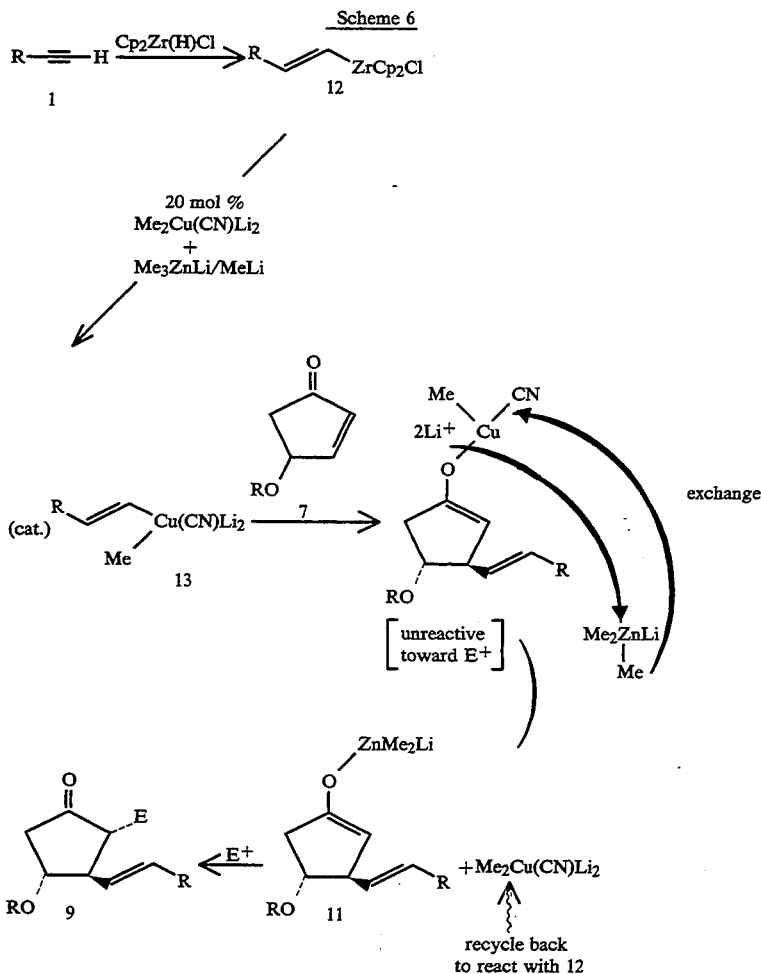

In accordance with the present invention, the aforesaid ligands $R_T$ and $R_E$, as well as the portions of the enone $R^A$ and $R^B$ which are not involved in the addition reaction, may be substituted by one or more non-interfering substituents. By non-interfering substituents is meant substituents which do not engage in undesirable side-reactions or rearrangements in the organometallic complexes, and which do not hinder reaction due to steric and/or electronic factors. For example, suitable non-interfering substituents include alkyl, phenyl, alkoxy, phenoxy, halogen, and protected hydroxy (i.e., a hydroxyl group which is protected by one of a variety of protective groups which are known per se) and the like. In addition, carbanions containing aldehyde, ketone and carboxyl functional groups which are suitably protected in a manner known per se may successfully be employed in accordance with the inventive method [see Schwartz et al., supra, at 339]. Typically, the substituents comprise lower alkyl groups or derivatives thereof, wherein lower alkyl represents straight- or branched-chain alkyl of one to six carbons or cycloalkyl of three to six carbon atoms. The presence of non-interfering substituents on other reactants employed in accordance with the inventive method has no adverse impact on the reaction mechanisms contemplated herein.

The product may be recovered using known methods. All reactions are preferably carried out under an inert atmosphere (e.g., argon).

The invention will be better understood by reference to the following examples which are intended for purposes of illustration and are not to be construed as in any way limiting the scope of the present invention, which is defined in the claims appended hereto.

EXAMPLE 1

Preparation of 3-(1-octen-1-yl)-4-isopropylcyclohexanone

A 10 mL round-bottom flask equipped with a stir bar was charged with zirconocene chloride hydride (0.267 g, 1.014 mmol) and sealed with a septum. The flask was evacuated with a vacuum pump and purged with argon, the process being repeated 3 times. THF (2.5 mL) was injected and the mixture stirred to generate a white slurry which was treated via syringe with 1-octyne (0.113 g, 1.01 mmol). The mixture was stirred for 15 minutes to yield a yellow-green solution which was cooled to $-78°$ C. and treated via syringe with ethereal MeLi (0.63 mL, 1.01 mmol) to generate a dark red solution. Concurrently, CuCN (2.3 mg, 0.026 mmol) was placed in a 5 mL round-bottom flask equipped with a stir bar, and sealed under septum. The flask was evacuated and purged with argon as above and THF (0.5 mL) added via syringe. The resulting slurry was cooled to $-78°$ C. and treated with $ZnMe_2$ in heptane (0.43 mL, 0.52 mmol). To this slurry at $-78°$ C. was then added MeLi in $Et_2O$ (0.355 mL, 0.57 mmol). After 5 minutes the slurry was warmed to 0° C. for 10 minutes to afford a clear, colorless two-phase mixture, which was then cooled to −78° C. The solution of the zirconocene was added via canula to the Me$_2$Cu(CN)Li$_2$/ZnMe$_3$Li solution, thereby providing a reaction mixture comprising 5 mol-% of copper per mole of zirconium. The mixture was stirred for 15 minutes at −78° C. to yield a dark red solution which was treated with 4-isopropyl-2-cyclohexenone (77 μL, 0.5 mmol) as a neat liquid over 70 minutes. After 2 hours of additional stirring the mixture was quenched with 5 mL of 10% NH$_4$OH in saturated NH$_4$Cl. The product was extracted with 3×20 mL of ether and dried over Na$_2$SO$_4$. The solution was then filtered through flitted filter paper and the solvent removed in vacuo. The resulting residue was submitted to flash chromatography on silica gel (Petroleum Ether/Ethyl Acetate, 40/1) to give an 81% yield (101.8 mg) of 3-(1-octen-1-yl)-4-isopropylcyclohexanone as a colorless oil which gave satisfactory IR, NMR, MS, and HRMS data.

EXAMPLE 2

Preparation of 2-(1-hydroxyhexyl)-3-(1-octen-1-yl)-4-isopropyl cyclohexanone

Following the procedure of Example 1, a mixed solution was formed of the cuprate and Me$_3$ZnLi (0.52 mmol) comprising 10 mol-% of copper per mole of enone. The solution was treated with 4-isopropyl-2-cyclohexenone (77 μL, 0.5 mmol) as a neat liquid over 70 minutes and then stirred for an additional 2 hours. Hexanal (0.25 mL, 2.0 mmol), in 1.0 mL THF at −78° C., was then added. After 5 minutes the mixture was quenched with 5 mL of 10% NH$_4$OH in saturated NH$_4$Cl. The product was extracted with 3×20 mL of ether and dried over Na$_2$SO$_4$. The solution was then filtered through flitted filter paper and the solvent removed in vacuo. The resulting residue was submitted to flash chromatography on silica gel (Petroleum Ether/Ethyl Acetate, 30/1) to give an 82% yield of 2-(1-hydroxyhexyl)-3-(1-octen-1-yl)-4-isopropyl cyclohexanone as a colorless oil which gave satisfactory IR, NMR, MS, and HRMS data.

For purposes of comparison, a similar reaction sequence was carried out omitting the Me$_3$ZnLi and using 2 equivalents of cuprate (rather than 0.1 equivalent). The yield of product after addition of hexanal was only 63%.

EXAMPLE 3

Preparation of 3-(1-octen-1-yl)-4-isopropylcyclohexanone

A 10 mL round-bottom flask equipped with a stir bar was charged with zirconocene chloride hydride (0.301 g, 1.04 mmol) and sealed with a septum. The flask was evacuated with a vacuum pump and purged with argon, the process being repeated 3 times. THF (4 mL) was injected and the mixture stirred to generate a white slurry which was treated via syringe with 1-octyne (0.115 g, 1.04 mmol). The mixture was stirred for 15 minutes to yield a yellow-to-green solution which was cooled to −78° C. and treated via syringe with ethereal MeLi (0.65 mL, 1.03 mmol) to generate a dark red solution. At the same time, a 5 mL flask with septum was purged as above with Ar and then 1 mL of THF was added via syringe. To this flask at −78° C. was added ZnMe$_2$ in heptane (0.44 mL, 0.53 mmol), followed by MeLi in Et$_2$O (0.33 mL, 0.53 mmol). After 5 minutes the solution was warmed to 0° C. for 10 minutes to afford a clear solution, which was then cooled to −78° C. Concurrently, CuI (20.7 mg, 0.109 mmol) was placed in a 10 mL round-bottom flask equipped with a stir bar, and sealed under septum. The flask was evacuated and purged with argon as above and THF (1 mL) added via syringe. To this slurry at −78° C. was then added MeLi in Et$_2$O (0.136 mL, 0.217 mmol). The slurry was warmed slightly to generate a clear solution of Me$_2$CuLi, then cooled to −78° C. At −78° C. and by cannula the solution of Me$_3$ZnLi was added to the Me$_2$CuLi solution. The solution of the zirconocene was added via cannula to the resulting Me$_2$CuLi/Me$_3$ZnLi solution, thereby providing a reaction mixture comprising 20 mol-% of copper per mole of substrate enone. The mixture was stirred for 15 minutes at −78° C. to yield a dark red solution which was treated with 4-isopropyl-2-cyclohexenone (77 μL, 0.5 mmol) as a neat liquid over 70 minutes. After 1 hour of additional stirring the mixture was quenched with 5 mL of 10% NH$_4$OH in saturated NH$_4$Cl. The product was extracted with 3×20 mL of ether and dried over Na$_2$SO$_4$. The solution was then filtered through fritted filter paper and the solvent removed in vacuo. The resulting residue was submitted to flash chromatography on silica gel (Petroleum Ether/Ethyl Acetate 40/1) to give a 92% yield (115.3 mg) of the product as a colorless oil giving satisfactory IR, NMR, MS and HRMS data.

EXAMPLE 4

Preparation of 3-(1-octen-1-yl)-4-isopropylcyclohexanone

A 10 mL round-bottom flask equipped with a stir bar was charged with zirconocene chloride hydride (0.305 g, 1.07 mmol) and sealed with a septum. The flask was evacuated with a vacuum pump and purged with argon, the process being repeated 3 times. THF (4 mL) was injected and the mixture stirred to generate a white slurry which was treated via syringe with 1-octyne (0.115 g, 1.04 mmol). The mixture was stirred for 15 minutes to yield a yellow-to-green solution which was cooled to −78° C. and treated via syringe with ethereal MeLi (0.63 mL, 1.01 mmol) to generate a dark red solution. At the same time, NiCl$_2$ (68 mg, 0.52 mmol) was placed in a 5 mL round bottom flask and purged as above with Ar to which was added 1 mL THF via syringe. This solution was then cooled to −78° C. where it was treated with MeLi in Et$_2$O (0.98 mL, 1.574 mmol) and then warmed to about −20° C. for 10 minutes to generate a dark brown solution. It was then cooled again to −78° C. Concurrently, CuCN (9.3 mg, 0.104 mmol) was placed in a 10 mL round-bottom flask equipped with a stir bar and sealed under septum. The flask was warmed slightly to generate a clear solution of Me$_2$Cu(CN)Li$_2$, then cooled to −78° C. At −78° C. and by cannula the solution of NiMe$_3$Li was added to the Me$_2$Cu(CN)Li$_2$ solution. The solution of the zirconocene was added via cannula to the resulting Me$_2$Cu(CN)Li$_2$/NiMe$_3$Li solution, thereby providing a reaction mixture comprising 20 mol-% of copper per mole of substrate enone. The mixture was stirred for 15 minutes at −78° C. to provide a dark brown solution, which was treated with 4-isopropyl-2-cyclohexenone (77 μL, 0.5 mmol) added slowly as a neat liquid over 70 minutes. After stirring for 1.5 hours, the mixture was quenched with 5 mL of 10% NH$_4$OH in saturated NH$_4$Cl. The product was extracted with 3×20 mL of ether and dried over Na$_2$SO$_4$. The solution was then filtered through fritted filter paper and the solvent removed in vacuo. The resulting residue was submitted to flash chromatography on silica gel (Petroleum Ether-/Ethyl Acetate, 40/1) to give a 77% yield (97.1 mg) of 3-(1-octen-1-yl)-4-isopropylcyclohexanone as a colorless oil giving satisfactory IR, NMR, MS and HRMS data.

EXAMPLE 5

Preparation of
E,E-3,6-dimethyl-8-oxo-deca-2,4-dien-1-ol tert-butyl dimethylsilyl ether

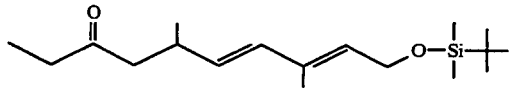

A 10 mL round-bottom flask equipped with a stir bar was charged with zirconocene chloride hydride (0.300 g, 1.012 mmol) and sealed with a septum. The flask was evacuated with a vacuum pump and purged with argon, the process being repeated 3 times. THF (4 mL) was injected and the mixture stirred to generate a white slurry which was treated via syringe with E-4-methyl-pent-2-en-4-yn-1-ol tertbutyl dimethylsilyl ether (0.215 g, 1.012 mmol). The mixture was stirred for 15 minutes to yield a yellow-to-green solution which was cooled to −78° C. and treated via syringe with ethereal MeLi (0.66 mL, 1.012 mmol) to generate a dark red solution. Concurrently, CuCN (9.5 mg, 0.106 mmol) was placed in a 10 mL round-bottom flask equipped with a stir bar and sealed under septum. The flask was evacuated and purged as above with Ar and then 1.5 mL of THF was added via syringe. The resulting slurry was cooled to −78° C. and treated with ZnMe$_2$ in heptane (0.43 mL, 0.53 mmol). To this slurry, still at −78° C., was then added MeLi in Et$_2$O (0.48 mL, 0.73 mmol). After 5 minutes the slurry was warmed to 0° C. for 10 minutes to afford a clear, colorless, homogeneous solution which was then cooled to −78° C. The solution of the zirconocene was added via cannula to the Me$_2$Cu(CN)Li$_2$/Me$_3$ZnLi solution, thereby providing a reaction mixture comprising 20 mol-% of copper per mole of substrate enone. The mixture was stirred for 15 minutes at −78° C. to yield a yellow solution which was treated with E-4-hexen-3-one (58 μL, 0.5 mmol) added as a neat liquid over 70 minutes. After 1 hour of additional stirring the mixture was quenched with 5 mL of 10% NH$_4$OH in saturated NH$_4$Cl. The product was extracted with 3×20 mL of ether and dried over Na$_2$SO$_4$. The solution was then filtered through fritted filter paper and the solvent removed in vacuo. The resulting residue was submitted to flash chromatography on silica gel (Petroleum Ether/Ethyl Acetate 50/1) to give an 86% yield (134 mg) of the product as a colorless oil giving satisfactory IR, NMR, MS and HRMS data.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method for sequential introduction of substituents to an enone by 1,4-conjugate addition to introduce a first substituent group R$_T$ and form an intermediate enolate, followed by electrophilic trapping of the enolate to introduce a second substituent group R$_E$, said method comprising:

forming a reactive cuprate solution comprising a catalytic amount of a reactive cuprate containing group R$_T$, and an organometallic compound comprising a metal which forms a more reactive enolate than a corresponding enolate derived from the cuprate;

reacting the reactive cuprate solution with the enone to introduce group R$_T$ and form a reactive enolate by exchange between copper and the organometallic compound; and trapping the reactive enolate with an electrophile precursor to R$_E$ to introduce group R$_E$, wherein R$_T$ is selected from the group consisting of alkyl of one to about 20 carbon atoms, cycloalkyl of three to about 20 carbon atoms, alkenyl of two to about 20 carbon atoms, cycloalkenyl of three to about 20 carbon atoms, aryl, allyl and benzyl, and R$_E$ is selected from the group consisting of alkyl of one to about 20 carbon atoms, cycloalkyl of three to about 20 carbon atoms, alkenyl of two to about 20 carbon atoms, cycloalkenyl of three to about 20 carbon atoms, aryl, allyl and benzyl, each of R$_T$ and R$_E$ being unsubstituted or substituted by one or more non-interfering substituents selected from the group consisting of alkyl of one to about six carbon atoms, phenyl, alkoxy of one to about six carbon atoms, cycloalkyl of three to about six carbon atoms, phenoxy, halogen, protected hydroxy, protected aldehyde, protected ketone and protected carboxyl.

2. A method according to claim 1, wherein said reactive cuprate comprises a compound of general formula I

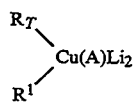

wherein R$^1$ is different from R$_T$ and is selected from the group consisting of alkyl, alkenyl, alkynyl, allylic, aryl, benzylic and heterocyclic moieties, —BR$^3$ wherein B is O or S and R$^3$ is an alkyl, alkenyl, alkynyl, allylic, aryl, benzylic or heterocyclic moiety, and —NR$^4$R$^5$ and —PR$^4$R$^5$ wherein R$^4$ and R$^5$ are the same or different and each is an alkyl, alkenyl, alkynyl, allylic, aryl, benzylic or heterocyclic moiety, said moieties being unsubstituted or substituted by non-interfering substituents; and A is CN or SCN.

3. A method according to claim 2, wherein said compound of general formula I is prepared by:

reacting a precursor to R$_T$ with Cp$_2$Zr(H)Cl and then R$^2$Li to form an intermediate zirconocene containing group R$_T$; and reacting the intermediate zirconocene with a catalytic amount of a cuprate source to form the reactive cuprate in the presence of the organometallic compound comprising a metal which forms a more reactive enolate to form the reactive cuprate solution.

4. A method according to claim 3, wherein said precursor to $R_T$ comprises an alkyne.

5. A method according to claim 1, wherein said reactive cuprate is a lower order copper complex.

6. A method according to claim 5, wherein said lower order copper complex is selected from the group consisting of $R_TR^1CuLi$, $R_TR_2^1Cu_2Li$ and $R_TR_4^1Cu_3Li_2$, wherein $R^1$ is different from $R_T$ and is selected from the group consisting of alkyl, alkenyl, alkynyl, allylic, aryl, benzylic and heterocyclic moieties, —$BR^3$ wherein B is O or S and $R^3$ is an alkyl, alkenyl, alkynyl, allylic, aryl, benzylic or heterocyclic moiety, and —$NR^4R^5$ and —$PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents.

7. A method according to claim 1, wherein said organometallic compound comprising a metal which forms a more reactive enolate than copper is selected from the group consisting of alkyl metal lithiums of formula $R_n^1MLi$, wherein M is a metal ion which forms an enolate which is more reactive toward electrophiles than the corresponding enolate derived from the cuprate, n is an integer corresponding to the oxidation state of the metal ion plus 1 and $R^1$ is different from $R_T$ and is selected from the group consisting of alkyl, alkenyl, alkynyl, allylic, aryl, benzylic and heterocyclic moieties, —$BR^3$ wherein B is O or S and $R^3$ is an alkyl, alkenyl, alkynyl, allylic, aryl, benzylic or heterocyclic moiety, and —$NR^4R^5$ and —$PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents.

8. A method according to claim 7, wherein M is selected from the group consisting of $Zn^{+2}$, $Mn^{+2}$, $Ni^{+2}$, $Sn^{+4}$, $Ti^{+4}$, $Fe^{+3}$, $Co^{+2}$, $Co^{+3}$, $Ag^{+1}$, $Ge^{+4}$, $Zr^{+4}$ and $Cd^{+2}$.

9. A method according to claim 1, wherein said catalytic amount of a reactive cuprate containing group $R_T$ comprises about 1 mol-% to about 20 mol-% based on the enone.

10. A method according to claim 1, wherein said precursor to $R_E$ is selected from the group consisting of compounds of the formula $R_EX'$, wherein $X'$ is a suitable leaving group; carbonyl compounds; acylating agents; α,β-unsaturated nitro compounds; epoxides; and vinyl sulfoxides and sulfones.

11. A method for 1,4-addition of a group $R_T$ to an enone, comprising:
   forming a reactive cuprate solution comprising a catalytic amount of a reactive cuprate containing group $R_T$, and an organometallic compound comprising a metal which forms a more reactive enolate than a corresponding enolate derived from the cuprate; and
   reacting the reactive cuprate solution with the enone to introduce group $R_T$,
wherein $R_T$ is selected from the group consisting of alkyl of one to about 20 carbon atoms, cycloalkyl of three to about 20 carbon atoms, alkenyl of two to about 20 carbon atoms, cycloalkenyl of three to about 20 carbon atoms, aryl, allyl and benzyl, $R_T$ being unsubstituted or substituted by one or more non-interfering substituents selected from the group consisting of alkyl of one to about six carbon atoms, phenyl, alkoxy of one to about six carbon atoms, cycloalkyl of three to about six carbon atoms, phenoxy, halogen, protected hydroxy, protected aldehyde, protected ketone and protected carboxyl.

12. A method according to claim 11, wherein said reactive cuprate comprises a compound of general formula I

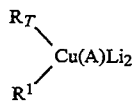

wherein $R^1$ is different from $R_T$ and is selected from the group consisting of alkyl, alkenyl, alkynyl, allylic, aryl, benzylic and heterocyclic moieties, —$BR^3$ wherein B is O or S and $R^3$ is an alkyl, alkenyl, alkynyl, allylic, aryl, benzylic or heterocyclic moiety, and —$NR^4R^5$ and —$PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents; and A is CN or SCN.

13. A method according to claim 12, wherein said compound of general formula I is prepared by:
   reacting a precursor to $R_T$ with $Cp_2Zr(H)Cl$ and then $R^2Li$ to form an intermediate zirconocene containing group $R_T$; and
   reacting the intermediate zirconocene with a catalytic amount of a cuprate source to form the reactive cuprate in the presence of the organometallic compound comprising a metal which forms a more reactive enolate to form the reactive cuprate solution.

14. A method according to claim 13, wherein said precursor to $R_T$ comprises an alkyne.

15. A method according to claim 11, wherein said reactive cuprate is a lower order copper complex.

16. A method according to claim 15, wherein said lower order copper complex is selected from the group consisting of $R_TR^1CuLi$, $R_TR_2^1Cu_2Li$ and $R_TR_4^1Cu_3Li_2$, wherein $R^1$ is different from $R_T$ and is selected from the group consisting of alkyl, alkenyl, alkynyl, allylic, aryl, benzylic and heterocyclic moieties, —$BR^3$ wherein B is O or S and $R^3$ is an alkyl, alkenyl, alkynyl, allylic, aryl, benzylic or heterocyclic moiety, and —$NR^4R^5$ and —$PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents.

17. A method according to claim 11, wherein said organometallic compound comprising a metal which forms a more reactive enolate than copper is selected from the group consisting of alkyl metal lithiums of formula $R_n^1MLi$, wherein M is a metal ion which forms an enolate which is more reactive toward electrophiles than the corresponding enolate derived from the cuprate, n is an integer corresponding to the oxidation state of the metal ion plus 1 and $R^1$ is different from $R_T$ and is selected from the group consisting of alkyl, alkenyl, alkynyl, allylic, aryl, benzylic and heterocyclic moieties, —$BR^3$ wherein B is O or S and $R^3$ is an alkyl, alkenyl, alkynyl, allylic, aryl, benzylic or heterocyclic moiety, and —$NR^4R^5$ and —$PR^4R^5$ wherein $R^4$ and $R^5$ are the same or different and each is an alkyl, alkenyl, alkynyl, allylic, aryl, benzylic or heterocyclic moiety, said moieties being unsubstituted or substituted by non-interfering substituents.

18. A method according to claim 17, wherein M is selected from the group consisting of $Zn^{+2}$, $Mn^{+2}$, $Ni^{+2}$, $Sn^{+4}$, $Ti^{+4}$, $Fe^{+3}$, $Co^{+2}$, $Co^{+3}$, $Ag^{+1}$, $Ge^{+4}$, $Zr^{+4}$ and $Cd^{+2}$.

19. A method according to claim 11, wherein said catalytic amount of a reactive cuprate containing group $R_T$ comprises about 1 mol-% to about 20 mol-% based on the enone.

* * * * *

UNITED STATES PATENT AND TRADEMARK OFFICE
CERTIFICATE OF CORRECTION

PATENT NO. : 5,405,981
DATED : April 11, 1995
INVENTOR(S) : Bruce H. Lipshutz

It is certified that error appears in the above-indentified patent and that said Letters Patent is hereby corrected as shown below:

Column 1, line 66, replace "EtO" with --$Et_2O$--.

Column 8, line 50, replace first instance of "$Co^{+3}$" with --$Co^{+2}$--.

Column 14, line 5, replace "proposes" with --purposes--.

Column 17, line 13, replace "flitted" with --fritted--.

Column 17, line 36, replace "flitted" with --fritted--.

Column 21, line 36, replace "$CO^{+2}$, $CO^{+3}$" with --$Co^{+2}$, $Co^{+3}$--.

Signed and Sealed this

Twenty-fifth Day of July, 1995

Attest:

BRUCE LEHMAN

Attesting Officer        Commissioner of Patents and Trademarks